United States Patent [19]
Firoozabady et al.

[11] Patent Number: 5,952,543
[45] Date of Patent: Sep. 14, 1999

[54] GENETICALLY TRANSFORMED PINEAPPLE PLANTS AND METHODS FOR THEIR PRODUCTION

[75] Inventors: Ebrahim Firoozabady, Pleasant Hill; Neal Gutterson, Oakland, both of Calif.

[73] Assignee: DNA Plant Technology Corporation, Oakland, Calif.

[21] Appl. No.: 09/028,936

[22] Filed: Feb. 24, 1998

Related U.S. Application Data

[60] Provisional application No. 60/039,092, Feb. 25, 1997.

[51] Int. Cl.[6] .............................. A01H 5/00; C12N 15/82; C12N 15/84; C12N 5/04

[52] U.S. Cl. .......................... 800/294; 800/278; 800/279; 800/283; 800/288; 800/290; 800/301; 800/302; 800/280; 800/284; 800/298; 435/419; 435/418; 435/430; 435/430.1; 435/431; 435/469

[58] Field of Search ................................ 435/69.1, 252.2, 435/418, 419, 430, 431, 469, 430.1; 536/23.6, 24.1; 800/279, 280, 283, 284, 288, 290, 294, 301, 302, 278, 298

[56] References Cited

U.S. PATENT DOCUMENTS

| | | | |
|---|---|---|---|
| 5,424,412 | 6/1995 | Brown et al. | 536/24.1 |
| 5,589,623 | 12/1996 | Ferro et al. | 800/283 |

FOREIGN PATENT DOCUMENTS

| | | | |
|---|---|---|---|
| WO 94/17194 | 8/1994 | WIPO | C12N 15/82 |

OTHER PUBLICATIONS

Gamborg, *Cell Culture and Somatic Cell Genetics of Plants*, 1984, vol. 1, "Plant Cell Cultures: Nutrition and Media," pp. 18–26.
Rangan, *Handbook of Plant Cell Culture*, 1984, vol. 3, Chapter 14, Pineapple, pp. 373–382.
Pena et al, Plant Cell Rep., vol. 14, pp. 616–619, 1995.
Chan et al, J. Biol. Chem., vol. 269, pp. 17635–17641, 1994.
Shcherban et al, Proc. Natl. Acad. Sci., USA, vol. 92, pp. 9245–9249, 1995.
Kleiner et al, Environ. Entomol., vol. 24, pp. 1358–1364, 1995.
Pilon–Smits et al, Plant Physiol., vol. 107, pp. 125–130, 1995.
Erion et al, Plant Physiol., vol. 97, pp. 1462–1469, 1991.
Culver et al, Mol. Plant Microbe Inter., vol. 4, pp. 458–463, 1991.
Chen et al, Plant Cell Rep., vol. 14, pp. 354–358, 1995.
Collins et al, Crop Sci., vol. 18, pp. 286–288, 1978.
Gatehouse et al, Entomol. Exp. Appl., vol. 54, pp. 43–51, 1990.

*Primary Examiner*—David T. Fox
*Assistant Examiner*—Ashwin D. Mehta
*Attorney, Agent, or Firm*—Townsend and Townsend and Crew

[57] ABSTRACT

The present invention is directed to methods for the genetic transformation of pineapple plant tissue with Agrobacterium. The present invention also provides for the regeneration of intact pineapple plants from the transformed tissue.

38 Claims, No Drawings ately at least 500 nucleotides in length. A DNA segment can be full-length or a subsequence of a structural or regulatory gene.
GENETICALLY TRANSFORMED PINEAPPLE PLANTS AND METHODS FOR THEIR PRODUCTION

CROSS REFERENCE TO RELATED APPLICATIONS

This is a continuation of U.S. Ser. No. 60/039,092, filed Feb. 25, 1997, which is incorporated herein by reference.

FIELD OF THE INVENTION

The present invention relates generally to methods for genetically transforming pineapple plants. The present invention also relates to transformed plants. More particularly, the invention relates to a method for genetically transforming and regenerating pineapple plants.

BACKGROUND OF THE INVENTION

Pineapple (Ananas spp.) is an important food crop. Many varieties of pineapple are used for human consumption, including Smooth Cayenne, Red Spanish, Perolera, Pernambuco, Primavera. The most important variety for use in production of canned pineapple, other processed pineapple products, and fresh pineapple is Smooth Cayenne. Within many varieties there are a large number of clones which have been established in different geographical areas, and which are adapted to production in those locations. Amongst the Smooth Cayenne clones are the Champaka clones which have been used extensively for production of canned and fresh pineapple.

Pineapple is self-incompatible with long periods between successive fruit generations. Consequently, conventional breeding to improve fruit quality has been difficult. Indeed, breeding as a means to develop varieties of pineapple has been generally unsuccessful. There are, however, many traits that would be of interest to introduce into specific pineapple varieties.

For example, it is desirable to introduce agronomic traits such as improved resistance to bacterial diseases, improved resistance to viral diseases, and improved resistance to insects and nematodes. In addition to agronomic traits, it is desirable to modify characteristics of the fruit of interest to consumers (consumer traits) of the fruit, such as sweetness, acidity, and texture. Further, it is desirable to control the ripening characteristics of the fruit. Because of the difficulties with breeding, genetic engineering offers important potential for the improvement of pineapple varieties.

SUMMARY OF THE INVENTION

The present invention provides methods for modifying the genotype of a pineapple (Ananas spp.) cell. The methods comprise contacting the pineapple cell with a culture of Agrobacterium comprising a T-DNA and selecting cells that contain the T-DNA. The T-DNA includes a DNA segment operably linked to a promoter and functional in the pineapple cell, such that the DNA segment is integrated into the genome of the pineapple cells. The DNA segment can comprise a gene, a gene fragment, or a combination of genes. In some embodiments the pineapple cell contacted with the culture of Agrobacterium is an embryogenic cell or an embryogenic callus cell. The pineapple is preferably selected from the group consisting of Smooth Cayenne, Red Spanish, Perolera, Pernambuco, and Primavera. Smooth Cayenne is particularly preferred. The Agrobacterium is preferably *Agrobacterium tumefaciens*. In some embodiments the method further comprises the step of regenerating a pineapple plant from the cell comprising the integrated DNA. The promoter can be constitutive, inducible, or tissue specific. In preferred embodiments the T-DNA comprises a selectable marker. In another aspect the present invention also relates to a pineapple cell, a pineapple plant, or a pineapple plant part (e.g., tissue or organ such as fruit) modified by the methods of the present invention.

In some embodiments, the pineapple cells to be transformed are embryogenic cells. The embryogenic cells can be, for instance, embryogenic cell clusters in friable callus or globular callus.

Generally, the pineapple tissue at the young shoot stage is cultured on a medium comprising an effective amount of a strong auxin such as picloram. In preferred embodiments the pineapple tissue is from a pineapple leaf base or a stem section. In yet a further aspect, the present invention relates to a pineapple cell modified by the aforementioned method.

In another aspect, the present invention is directed to a pineapple plant cell comprising an integrated Agrobacterium T-DNA sequence comprising a heterologous DNA segment. In some embodiments the heterologous DNA is operably linked to a constitutive promoter, in others to an inducible promoter, in still others to a tissue specific promoter. The DNA segment may be operably linked to the promoter in sense or antisense orientation. The heterologous DNA in the composition can be a selectable marker gene. In some embodiments, the cell is a tissue culture cell. In some embodiments the pineapple cell is Smooth Cayenne.

In an additional aspect the present invention is directed to a pineapple plant comprising an integrated Agrobacterium T-DNA sequence comprising a heterologous DNA segment. The heterologous DNA segment may confer resistance to insects, drought, nematodes, viral disease, bacterial disease, or may impart desired fruit traits. In some embodiments the pineapple plant is Smooth Cayenne.

DESCRIPTION OF THE PREFERRED EMBODIMENT

Definitions

Units, prefixes, and symbols can be denoted in their SI accepted form. Numeric ranges are inclusive of the numbers defining the range. The headings provided herein are not limitations of the various aspects or embodiments of the invention which can be had by reference to the specification as a whole. Accordingly, the terms defined immediately below are more fully defined by reference to the specification in its entirety.

As used herein, "DNA segment" includes reference to a deoxyribopolynucleotide or transcribable analogs thereof of at least 50 nucleotides in length, usually at least 100 nucleotides in length, generally at least 200 nucleotides in length, preferably at least 300 nucleotides in length, more preferably at least 400 nucleotides in length, and most preferably at least 500 nucleotides in length. A DNA segment can be full-length or a subsequence of a structural or regulatory gene.

As used herein, "contacting" includes reference to placement in direct physical association.

As used herein, "culture of Agrobacterium" includes reference to a composition comprising a species, subspecies, or strain of the bacterium Agrobacterium which is able to mobilize and selectively transfer T-DNA into a pineapple cell. The Agrobacterium may be *Agrobacterium rhizogenes*, preferably *Agrobacterium tumefaciens*.

As used herein, "T-DNA" includes reference to the segment of DNA which is mobilized and transferred from Agrobactelium into the plant cell which is thereby transformed.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the "leaf base" is that portion of the leaf which is connected to the stem of a shoot of pineapple.

An in vitro grown stem is referred to here as the "core".

An in vitro grown shoot includes reference to the core plus the leaves.

As used herein, "functional in the pineapple cell" includes reference to transcription of a DNA segment within the pineapple cell.

As used herein, "embryogenic cell" includes reference to a cell from embryogenic tissue or embryogenic callus.

The term "embryogenic tissue" refers to tissue comprising organized structures that include immature somatic embryos. Immature somatic embryos can be matured by culturing on a maturation medium. A mature somatic embryo can develop into plants upon transfer to a germination medium. A mature somatic embryo is an embryo with an elongated cotyledon.

The term "embryogenic callus" refers to tissue that is undifferentiated and without significant structure but with the potential to form a more differentiated tissue (e.g., embryogenic tissue) that can produce embryos and germinate into plants.

As used herein, "embryogenic cell cluster" includes reference to a pineapple tissue containing cell clusters with potential for somatic embryo production upon suitable hormone treatment. The cell clusters typically comprise from 20 to about 500 small cells of from about 5 to 10 $\mu$m in diameter.

As used herein "mature somatic embryo" is a structure ultimately derived from somatic cells that resembles a zygotic embryo morphologically and developmentally, and that is capable of germinating into a plantlet with both root and shoot poles, when transferred to a suitable growth medium.

As used herein, "somatic cell" is a cell of a multicellular organism other than gametes.

As used herein, "regenerating a pineapple plant" includes reference to the formation of a pineapple plant constituting a rooted shoot.

As used herein, "effective amount" includes reference to an amount sufficient to achieve a desired result such as the production of a callus or tissue which is embryogenic.

A polynucleotide sequence, such as a DNA segment, is "heterologous" to an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

Overview

The present invention provides genetically transformed pineapple plants obtained by the selective introduction of exogenous DNA segments into the chromosomes of pineapple cells. The methods include use of suitable pineapple explant material which is genetically transformed by contacting the explant material with Agrobacterium cells. The Agrobacterium cells mediate the transfer of a DNA segment into pineapple cells. The present invention also provides culture media suitable for the steps of inducing the formation of embryogenic cells for co-cultivation with Agrobacterium cells. Transformed embryogenic cells are selected and embryos are formed therefrom. The embryos can be germinated to form shoots and rooted to produce complete plants.

Source of Explant

Pineapple explant material can be obtained from a range of pineapple varieties. The specific variety of pineapple is not a critical feature of the present invention. Varieties which can be used include those of the Smooth Cayenne group (including Champaka clones), the Spanish group, the Perolera group, the Pernambuco group, and the Primavera group.

The initial explant can be any meristematic region of a plant, including either the main or axillary meristems (apices) of the plant prior to flower formation, and the main or axillary meristems of the crown of the fruit. These regions can be excised from the plant and sterilized by standard methods as described herein and well known to those of ordinary skill to establish sterile cultures in an artificial medium. Such cultures can be maintained for an extended period of time (e.g., weeks, months or years) by a series of propagation steps. Suitable media for establishment and maintenance of in vitro shoot cultures are described in the examples. See also, DeWald et al., *Plant Cell Reports,* 7:535–537 (1988).

In a preferred aspect of the present invention, the embryogenic cells which are the target for DNA delivery are first obtained from the basal portion of leaves (i.e., leaf base) or sections of the stem of pineapple shoots grown in vitro, and proliferated in culture prior to the DNA delivery step.

For induction of embryogenic callus or embryogenic tissue, sterile explants such as leaves or leaf bases are transferred onto specific artificial media as described herein. DNA can be delivered to the cells of the leaf, leaf base, or stem sections as they undergo embryogenesis, or DNA can be delivered to embryogenic cells immediately after they have given rise to embryogenic callus or tissue, or DNA can be delivered to embryogenic cells after the embryogenic material has been maintained in vitro for some period of time.

Types of Embryogenic Material

A range of embryogenic callus types and embryogenic tissue types, all of which are capable of producing embryos when exposed to suitable combinations of plant growth regulators under appropriate environmental conditions, can be used in the present invention. Specific pineapple cell types, in particular embryogenic tissue and embryogenic callus, are suitable targets for regeneration and transformation. Embryogenic callus is undifferentiated and without significant structure but with the potential to form a more differentiated tissue (i.e., embryogenic tissue), that can produce embryos and germinate into plants. Embryogenic tissue is a tissue containing organized structures that consist of immature somatic embryos. Pineapple embryogenic callus and embryogenic tissue are typically derived from maternal plant tissue and proliferated either on solid medium or in suspensions.

The relevant callus types are those from which embryogenic tissues can be derived. Either friable callus (i.e., easily dispersible) or globular callus (not readily dispersible) can be treated with specific hormone combinations to induce the formation of embryogenic tissue. Typically embryogenic tissue comprises a large number of embryo-like or embryoid structures. Thus the conversion of callus into embryogenic tissue is based on an increase in tissue organization, with callus having no organized structures. The more mature the embryos, the larger and more differentiated are the structures present in the embryogenic tissue. The types of embryogenic tissues that can be used in pineapple transformation range from very friable callus (comprising cell clusters with potential to produce embryos) to chunky (comprising relatively mature embryo-like structures). The most preferred type of embryogenic tissue is one which is highly friable and which contains embryogenic cell clusters (ECC) that, upon suitable hormone treatmuent—or series of treatments—can develop into mature somatic embryos.

Another preferred type of tissue is an embryogenic tissue in which the embryo structures in the tissue have matured further, to the globular stage, but they are still immature. This tissue type is known as friable embryogenic tissue (FET). In a more advanced stage of embryo development the tissue becomes chunky, and it is no longer friable. Such tissue is generally referred to as embryogenic tissue, or ET.

Embryogenic callus and embryogenic tissue are preferably derived from the basal portion of leaves of pineapple plantlets (leaf bases) growing in sterile culture. The embryogenic tissue produced from leaf bases can be proliferated on solid medium using a range of different plant hormone combinations.

One skilled in the art will recognize that the different types of embryogenic tissues described above, any of which can be used as the target tissue for DNA delivery and selection of transformation events, also represent stages of maturation towards the production of whole transgenic pineapple plants. For example, embryogenic cell clusters can be induced to form friable embryogenic tissue, which in turn can be induced to form embryogenic tissue, which in turn can be induced to form mature somatic embryos which can be germinated to produce pineapple plantlets. The successive conversion steps are controlled by altering the composition of the growth medium, particularly with respect to plant growth regulators and sugars as described in detail below.

In a preferred embodiment, friable callus is derived from leaf bases or stem sections of in vitro-propagated shoots. The friable callus is then induced to form globular somatic embryos directly, from which embryogenic tissue is derived. Upon a further modification of the culture medium, friable embryogenic tissue is derived which can be further converted into embryogenic cell clusters. The embryogenic cell clusters are cocultivated with Agrobacterium containing desirable DNA fragments engineered for transfer. Upon selection of transformed embryogenic cell clusters, a series of culture medium changes leads to the formation, in succession, of friable embryogenic tissue, embryogenic tissue, mature somatic embryos, shoots and plants. Transgenic plants produced in this way can be transferred to soil and grown in a greenhouse.

Media for Deriving and Manipulating Embryogenic Tissues

In order to produce the range of tissues or callus types that are embryogenic or potentially embryogenic it is necessary to culture the leaf base explants on specific combinations of plant hormones, and to culture the derived tissue or callus on media with yet other combinations of plant hormones. The production of callus from pineapple leaf bases is induced using media containing a strong synthetic auxin or a strong synthetic auxin in combination with a cytokinin. Most preferably the strong synthetic auxin will be picloram (4-amino-3,5,6-trichloro-2-pyridinecarboxylic acid) or dicamba (3,6-dichloro-2-methoxybenzoic acid), but other strong auxins including, but not limited to, 2,4-D (2,4-dichlorophenoxyacetic acid), NAA (naphthalene acetic acid) and NOA (naphthoxyacetic acid). Typically the auxin will be present at a concentration between about 1 mg/L to about 100 mg/L, preferably between about 5 mg/L to about 10 mg/L.

The cytokinins that can be used in combination with the strong synthetic auxin include, but are not limited to, BA (benzyl adenine), BAP (benzyl aminopurine), TDZ (thidiazuron), zeatin and kinetin. Typically the cytokinin will be present at a concentration between about 0.1 mg/L and about 10 mg/L, preferably between about 0.2 mg/L and about 5 mg/L. These can also be used at a wide range of effective concentrations, in part dependent upon the concentration of auxin used.

Once derived, embryogenic tissues can be maintained and proliferated on media containing hormone combinations similar to those used to derive the embryogenic tissue. A strong auxin is always necessary, and it may be used in combination with a cytokinin.

One of the preferred tissue types, ECC (embryogenic cell clusters), can be derived from more highly structured embryogenic tissue by culturing the embryogenic tissue on medium containing an auxin in combination with a gibberellin antagonist. A gibberellin antagonist useful in the invention can be ancymidol, or ABA (abscisic acid). A range of effective combinations of the gibberellin action inhibitors is exemplified below but is typically between about 0.01 mg/L and about 25 mg/L, preferably between about 0.05 mg/L and about 10 mg/L. The use of ECC is preferred for selection of transgenic tissue. Once transgenic tissues are derived, ECC can be induced to form a more mature form of embryogenic tissue, from which embryos and plants can be derived by a number of means, including but not limited to, removal of the gibberellin antagonist or ABA from the media, and/or by increasing sucrose concentration.

Mature embryos can be produced from embryogenic tissue by transferring embryogenic tissue onto a medium lacking auxin. For purposes of this disclosure, a medium lacking auxin or other plant growth regulator is one having less than about 1 mg/L, preferably less than about 0.5 mg/L. The media may have low levels of a cytokinin (such as those disclosed herein) or of a cytokinin in combination with low levels of an auxin such as NAA or IAA. As used herein, low levels of a particular plant growth regulator are those between about 0.5 mg/L and about 3 mg/L. The emerging shoots can be matured further by culturing on media lacking plant hormones. Using the above, one of skill can readily optimize effective amounts of various plant growth regulators by assaying for mature embryo production on a given media.

Methods of DNA Delivery

In one embodiment of the method, heterologous DNA sequences are to be introduced using Agrobacterium strains carrying the exogenous DNA in a T-DNA element. The recombinant T-DNA element can either be part of a Ti-plasmid that contains the virulence functions necessary for DNA delivery from Agrobacterium cells to plant cells, or the T-DNA element can be present on a plasmid distinct from another plasmid carrying the virulence functions (referred to as binary vectors). A variety of these binary vectors, capable of replication in both *E. coli* and Agrobacterium, have been described for this purpose. In a preferred method of co-cultivation Agrobacterium is grown to a concentration of $2-7\times10^8$ cells/ml and is diluted to $1-6\times10^8$ cells/ml, preferably $2-5\times10^8$ cells/ml before co-cultivation. Agrobacterium is co-cultivated for 2–5 days, preferably for 2–3 days with pineapple tissues.

Suitable Agrobacterium strains include *Agrobacterium tumefaciens* and *Agrobacterium rhizogenes*. While wild type strains may be used, "disarmed" derivatives of both species, in which the tumor-inducing sequences of the Ti plasmid have been removed, are preferred. Suitable *Agrobacterium tumefaciens* strains include EHA101, as described by Hood et al. (*J. Bacteriol.*, 168: 1291–1301, 1986), LBA4404, as described by Hoekema et al. (*Nature*, 303: 179–80,1983), and C58(pMP90), as described by Koncz and Schell (*Mol. Gen. Genet.*, 204, 383–96, 1986). A preferred *Agrobacterium rhizogenes* strain is 15834, as described by Birot et al. (*Biochem*, 25: 323–35).

The pineapple ET or callus and the Agrobacterium cells carrying the DNA segment are cocultivated in a suitable co-cultivation medium to allow transfer of the T-DNA to plant cells. After the Agrobacterium strain carrying the DNA segment has been prepared, it is usually cultured prior to incubation with the callus or embryogenic tissue. Agrobacterium can be cultured on solid or liquid media according to methods well known to those of skill in the art. See, U.S. Pat. No. 5,262,316.

DNA Constructs and Selection

The DNA segment to be introduced may be obtained from virtually any source, including bacterial, algal, fungal, foreign plant, endogenous pineapple plant, and animal, and will usually include at least one selectable plant marker gene to permit screening and selection of transformed cells (i.e., those cells which have incorporated the DNA segment into their chromosomes), as well as one or more functional genes which are chosen to provide, enhance, suppress, or otherwise modify expression of a desired trait or phenotype in the resulting plant. Exemplary DNA segments or genes of interest can be obtained from such well known genes as: ACC synthases, ACC oxidases, malic enzyme genes, malic dehydrogenases, glucose oxidases, chitinases, defensins, expansins, hemicellulases, xyloglucan transglycosylases, apetala genes, leafy genes, knotted-related genes, homeobox genes, Etr-related genes, and ribonucleases (e.g., barnase). A "gene of interest" includes reference to a structural gene which provides the transformed pineapple cell with desired characteristics. The "gene of interest" may have a coding sequence and be native (i.e., endogenous) to the pineapple plant or a heterologous gene.

A number of DNA constructs can be used in a number of techniques to suppress expression of endogenous plant genes, e.g., sense or antisense suppression or ribozymes. Anti-sense RNA inhibition of gene expression has been shown; see, e.g., Sheehy et al., *Proc. Nat. Acad. Sci. USA*, 85:8805–8809 (1988), and Hiatt et al., U.S. Pat. No. 4,801, 340. For examples of the use of sense suppression to modulate expression of endogenous genes see, Napoli et al., *The Plant Cell* 2:279–289 (1990), and U.S. Pat. No. 5,034, 323.

Catalytic RNA molecules or ribozymes can also be used to inhibit gene expression. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585–591 (1988).

For antisense suppression, the introduced sequence also need not be full length relative to either the primary transcription product or fully processed MRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

The introduced DNA sequences may also contain one or more functional genes that are chosen to provide a new plant trait, to enhance an existing plant trait, or to otherwise modify expression of plant phenotypes exhibited by the plant. Such traits include herbicide resistance, pesticide resistance, disease resistance, environmental tolerance (e.g., heat, cold, drought, salinity), morphology, growth characteristics, nutritional content, taste, yield, horticultural characteristics, consumer (quality) traits, and the like. Examples of genes that can be introduced include those to confer resistance or to reduce susceptibility to particular diseases or pests of pineapple. Examples include those reducing susceptibility to Fusariosis, mealy bug wilt, marbling disease, and nematodes.

A functional gene to be introduced may be a structural gene which encodes a polypeptide which imparts the desired phenotype. Alternatively, the functional gene may be a regulatory gene which might play a role in transcriptional and/or translational control to suppress, enhance, or otherwise modify the transcription and/or expression of an endogenous gene within the plant. It will be appreciated that control of gene expression can have a direct impact on the observable plant characteristics.

Often the functional genes to be introduced will be modified from their native form. For example, sense and anti-sense constructs referred to above often have all or a portion of the transcript of the native gene operably linked to a promoter sequence at the 5' end of the transcribable segment, and operably linked to the 3' sequence of another gene (including polyadenylation sequences) at the 3' end of the transcribable segment. As is apparent to those skilled in the art, the promoter sequence could be one of the many plant active sequences already described. Alternatively, other plant-active promoter sequences could be derived specifically to be linked to the transcribable segment. The promoter can be endogenous to pineapple, or can be from an exogenous source such as a cauliflower mosaic virus 35S promoter (Odell et al., Nature 313:810–812 (1985)), the ubiquitin 1 promoter, or the Smas promoter. The 3' end sequence to be added can be derived from, preferably, the nopaline synthase or octopine synthase genes, or alternatively from another plant gene, or less preferably from any other eukaryotic gene.

A preferred method of the invention is the use of Agrobacterium cells, carrying a heterologous DNA sequence which typically includes a plant selectable marker gene as well as one or more genes to be expressed, for introduction of DNA into pineapple embryogenic callus or tissue. The selectable plant marker gene on the DNA sequences to be inserted will usually encode a function which permits the survival and emergence of transformed embryogenic tissue or callus in a selective medium. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes icoding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron. Selection based on resistance to sulfonylurea-type herbicides is preferred.

Methods to select transformed plant cells incorporating a desired resistance gene are well known in the art. For example, if the marker is sulfonylurea resistance, the selection medium generally contains a sulfonylurea-type herbicide at an appropriate concentration (e.g., chlorosulfuron in the range of 5–1000 mg/l preferably about 10–100 mg/l). For selection of kanamycin resistant pineapple cells or tissue which contain the NPTII gene, kanamycin is typically included in the medium at 100–500 mg/l. Spectinomycin resistance cells or tissue containing the aadA gene are typically selected on medium containing 200–1000 mg/l spectinomycin.

Structural and regulatory genes to be inserted may be obtained from depositories, such as the American Type Culture Collection, Rockville, Md. 20852, as well as by isolation from other organisms, typically by the screening of genomic or cDNA libraries using conventional hybridization techniques, such as those described in Maniatis et al., Molecular Cloning A Laboratory Manual, Cold Spring Harbor Laboratory, Cold Spring Harbor, N.Y. (1985). Screening may be performed by (1) nucleic acid hybridization using homologous genes from other organisms, (2) probes synthetically produced to hybridize to particular sequences coding for desired protein sequences, or (3) DNA sequencing and comparison to known sequences. For the isolation of gene fragments to create anti-sense or sense transgenes for suppression of gene function, the polymerase chain reaction may be used, employing primers whose sequences are based on highly conserved sequences of the target gene. Sequences for specific genes may be found in various computer databases, including GeneBank, National Institutes of Health, as well as the database maintained by the U.S. Patent Office. The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. A mutant gene is isolated in which a transposon has inserted into the target gene and has altered the resulting phenotype. Using a probe for the transposon, the mutated gene can be isolated. Then, using the DNA adjacent to the transposon in the isolated, mutated gene as a probe, the normal wild-type allele of the target gene can be isolated. Such techniques are taught, for example, in McLaughlin and Walbot (1987) *Genetics*, 117:771–776; Dooner et al. (1985) *Mol. Gen. Genetics*, 200:240246; and Federoff et al. (1984) *Proc. Natl. Acad. Sci. USA*, 81:3825–3829, the disclosures of which are incorporated herein by reference.

In addition to the functional gene and the selectable marker gene, the DNA sequences may also contain a reporter gene which facilitates screening of the transformed shoots and plant material for the presence and expression of the DNA segment. Exemplary reporter genes include β-glucuronidase, luciferase and green fluorescent protein.

Regeneration of Pineapple Plants

After delivery of DNA, the embryogenic callus or tissue is transferred to medium containing a selective agent that is capable of preventing the growth of pineapple cells that have not received a gene whose product is capable of preventing the action of the selective agent (a selectable marker). After a period of culture, embryogenic callus or tissue that continues to grow normally is separated from embryogenic callus or tissue whose growth has been slowed or terminated.

After obtaining transformed embryogenic callus form non-transformed embryogenic callus the callus is transferred to embryo formation medium on which the transformed callus is converted into transformed embryogenic tissue. The embryo formation medium is a medium containing induction agents that are growth regulators, and sugar. Preferably, the embryo formation medium comprises picloram as an auxin with or without TDZ as a cytokinin, and sucrose as a sugar source. Typically, the auxin will be present at a concentration of between 1 mg/L and 100 mg/L, preferably between 5 mg/L and 10 mg/L; the cytokinin will be present at a concentration between 0.1 mg/L and 10 mg/L, preferably between about 0.1 mg/L and 5 mg/L; the sugar will be present at a concentration between about 30 g/L and 120 g/L, preferably between 45 g/L and 75 g/L. Transformed embryogenic tissue, whether produced from nontransformed embryogenic tissue or from transformed embryogenic callus, is transferred to a maturation medium leading to the production of mature embryos. Upon transfer to a germination medium, the mature embryos germinate into shoots or plants. The embryo maturation/germination medium is a medium comprising cytokinins and auxins. Typically, the maturation/germination medium comprises BA as a cytokinin, and NAA as a preferred auxin. Preferably, the cytokinin will be present at a concentration between about 0.5 mg/L and 5 mg/L, more preferably between about 1 mg/L and about 3 mg/L; the auxin will generally be present at about 0 mg/L and 1 mg/L, and most preferably between 0.1 mg/L and 0.5 mg/L. The shoots are transferred to a rooting medium to produce whole plants. The rooting medium comprises auxins. A rooting medium further comprising NAA and/or IBA is preferred. Typically, NAA or IBA will be present at a concentration between about 0.1 mg/L and 5 mg/L, preferably between about 0.2 mg/L and 1.0 mg/L. Whole, mature transformed pineapple plants can be obtained by transferring rooted plantlets expressing introduced DNA sequences into soil.

Although the present invention has been described in some detail by way of illustration and example for purposes of clarity of understanding, it will be obvious that certain changes and modifications may be practiced within the scope of the appended claims.

EXAMPLE 1

Transformation of Pineapple 1C Using *Agrobacterium tumefaciens* Strain C58pmp90/pNPT0502.

1. Preparation of source tissues.

(i) Establishment of shoot cultures.

Crown tip meristems isolated from crown of Smooth Cayenne pineapple fruits were used to establish shoot cultures. Briefly, leaves of the crown were removed by hand and discarded, the core or the stem of the crown (~3×5 cm) was surface sterilized with 20% CLOROX (sodium hypochlorite solution) with stirring for 20 min. and rinsed twice in sterile water, and the crown tip meristem was excised from the core by removing primary leaves one by one, while flaming the tools frequently. The crown tip meristem explant including the meristem dome, 2–3 tiny primary leaves, and 1 cm³ of the stem core was placed on the shoot culture medium B2N2. One week after culture initiation, the meristem had elongated and the primary leaves had opened fully. After four weeks when the primary leaves had grown to 10–15 mm, the explants were cut asymmetrically into two pieces to induce bud formation and plated on fresh B2N2 medium. Alternatively, six weeks after culture initiation the crown tip shoot was cut longitudinally into 2–4 sections, depending on the size of the shoots, and sections were cultured horizontally on B2N2 medium. After two additional weeks, buds were formed (3–5 per explant) and subsequently new small shoots were produced to form a cluster of shoots. Higher number of shoots were obtained with longitudinal or asymmetrical sectioning than normal procedure (respectively 30, 12, or 5 shoots per crown tip meristem were obtained within 8 weeks). At this point, shoot clusters were transferred and maintained in liquid MSB1.5N.5 medium in GA-7 boxes with biweekly subculture. In each subculture, shoot clusters were cut into several small clusters each with 3 shoots and then transferred to fresh medium. In B1.5N.5 medium shoots were multiplied at high frequencies. Typically within 4 weeks 12–15 shoots were obtained from a single shoot cluster cultured.

(ii) Production of embryogenic cell clusters (ECC) and other types of embryogenic tissues.

Shoots or shoot buds were used as explants. Tips of the long leaves (>15 mm) were cut off to provide smaller explants and to induce callus or embryogenic tissue formation. Shoots were cut longitudinally into 2–8 sections, depending upon their size, and placed horizontally on solid pretreatment medium MCMP10, MCMP10B.5, MSP10, or MSP10B.5. After 7–14 days on pretreatment medium, leaves were isolated and plated on different induction media (Table 1) to produce embryogenic callus. After 4 weeks on induction media, friable calli and embryonic tissues were produced on the base of leaf explants. All embryogenic tissues from MCM based media were transferred to MCMP10 and all embryogenic tissues from MS based media were transferred to MSP10 with the exception of those tissues from MSP10T2.2Agar in which one half of the tissues were also transferred to MCMP10. Four weeks later, all friable embryogenic tissues (FET) and embryogenic tissues (ET) were isolated from non-embryogenic tissues and were transferred to MCMP10. FET and ET were maintained on MCMP10 medium with monthly subculture for 3 months then on BacP10 medium with monthly subculture for an additional 9 months. During the maintenance, a portion of tissue developed into friable calli (FC) that was usually discarded when FET or ET were subcultured. In order to produce a suitable tissue for transformation and selection, ECCs or FETs were transferred to different media (Table 2). The medium BacP10ABA.05 produced the maximum amount of ECC. Subsequently, ECCs were maintained on this medium or Bac P10 medium with monthly subculture.

TABLE 1

Different induction media used for somatic embryogenesis of different lines of pineapple Overall rate of somatic embryogenesis (%)

| Induction media | |
|---|---|
| MCMP10TDZ2.2 | 31 |
| MCMP10TDZ1.1 | 28 |
| MCMP10B0.5 | 10 |
| MSP10TDZ2.2 | 34 |
| MSP10TDZ2.2Suc6O | 27 |
| MSP10TDZ2.2Agar | 55 |
| Pineapple lines | |
| 3A | 40 |
| 4A | 30 |
| 1C | 33 |
| 2C | 35 |
| 3C | 52 |

TABLE 2

Media used for production of ECC with different concentrations of different supplements

| Medium | Supplement | Suppl. conc. (mg/l) | | | |
|---|---|---|---|---|---|
| BacP10 | ABA | 0.02 | 0.05 | 0.20 | 2.00 |
| BacP10 | Ancymidol | 0.25 | 0.75 | 2.00 | 10.00 |
| BacP10 gelrite 1.5 | Ancymidol | 0.25 | 0.75 | 2.00 | 10.00 |
| Bac | Pic | 1 | 10 | | |
| BacP1 | 2,4-D | 1 | 5 | | |
| MSP10S60 | ABA | 0.05 | 0.20 | 2.00 | |
| MSP10S60 | Ancymidol | 0.25 | 2.00 | 10.00 | |
| MSP10 | Sucrose | 30,000 | 60,000 | 90,000 | 120,000 |

2. *Agrobacterium tumefaciens* culture and preparation.

*Agrobacterium tumefaciens* strain C58pmp90/pNPT0502 was used for inoculation. pNPT0502 contains the ubiquitin 1 promoter (Christensen et al., *Plant Mol. Biol.*, 18:675–689 (1992)) driving the neomycinphosphotransferase II gene, which confers paromomycine and geneticin (G418) resistance in the plant cells and the Smas promoter (Ni et al., *The Plant Journal*, 7:661–676 (1995)) driving an intron-containing β-glucuronidase gene. The β-glucuronidase gene contains an intron to prevent its expression in the bacteria. Bacteria were taken out of frozen glycerol, cultured and maintained on L-Broth medium solidified with 1.5% Bactoagar containing 10 mg/l tetracycline. One day before cocultivation, bacteria were scraped off the solid medium using a loop and suspended in liquid MinAsuc medium and cultured for one day on a shaker (120 rpm) at 28° C. Bacterial concentration was determined using a spectrophotometer (Perkin-Elmer Lambda 5) before cocultivation. The bacteria were cultured to an $OD_{550nm}$ of 0.662 and diluted to an $OD_{550nm}$ of 0.200 ($2\times10^8$ cells/ml) before inoculation.

3. Cocultivation on cocultivation medium.

Bacteria were mixed at the volume ratio of 1:5 (plant cell: Agrobacterium cell) with 0.8 gm/treatment of ECC. ECC was blotted dry and the mixture was placed on 7.0 cm sterile Fisherbrand G6 glass filter circles on the top of cocultivation medium BacP10ABA.05As100. Plates were parafilmed and placed in a 24° C. controlled environment incubator in the dark for 2 days.

4. Recovery and selection.

After cocultivation, tissues were transferred (20–25 pieces/plate, 48 pieces total, each piece weighed 20–50 mg) to selection medium BacPic10ABA.05Cef500 medium containing 50 (P50), 100, or 200 (P200) mg/l paromomycin for 11 days then to BacPic10ABA.05Cef500G10 for 3 weeks and to BacPic10ABA0.5Cef500G15 for 8 weeks. Cefotaxime was used to kill off the residual Agrobacterium, and paramomycin and G418 to select for transformed cells. On G418 containing selection media, most of the tissues turned brown within 11 weeks, however some sectors of the tissues remained healthy and appeared to be resistant to G418. These tissues were subsequently transferred to BacPic10ABA.05Cef500G30 for 4 weeks and then to BacPic10. Cef100G30 for selection and maintenance thereafter.

5. Confirmation of putative transformed tissues.

Putative G418–30 resistant calli were sampled (5–10 mg/resistant piece) for GUS assay according to standard techniques. Transformed cells stained blue and nontransformed cells did not stain blue. Four resistant ECC lines (3 from PSO and 1 from P200 treated tissues) were fully transformed.

6. Production of globular embryos and regeneration of transgenic shoots.

After 4 weeks on BacP10Cef100G30 and 4 weeks on BacP10S60 medium, resistant calli produced yellowish tissues with globular structures. The resistant globular structures were transferred to embryo formation medium BacS60B.5 medium for 8 weeks followed by transfer on maturation/germination medium MSB1 for 10 weeks to produce transgenic shoots. The shoots were vitrified (shoots with glossy and leathery leaves and high in water content). These were normalized by culturing for 4 weeks on MSB1Agar1% medium in plates and sealing with micropore tapes.

7. Micropropagation and production of transgenic plants.

Transgenic shoot clusters were transferred to 30 ml liquid MSB1 medium in 1000 ml beakers (5–6 clusters/beaker) for 4 weeks then MSB1.5N.5 medium for 4–10 weeks to elongate and multiply. Then individual shoots (4–5 cm long) were separated and cultured in liquid rooting medium N.5IBA.5 for 2–4 weeks to produce complete plants. Plants were transplanted in soil, hardened off gradually and then transferred to the greenhouse conditions. Out of 88 plants transplanted 75 plants were established in soil (establishment frequency=85%). These plants represent 5 transgenic lines.

8. Confirmation of transformation.

Transformation was confirmed by several means:

1) Transformed tissues continued their growth on the media with 25 ppb CS, whereas nontransformed control calli turned brown and eventually died. 2) Transformed calli, somatic embryos, leaf sections and roots from transformed plantlets all tested positive in the GUS assays. 3) The presence of the introduced gene by PCR in the embryogenic tissue and regenerated shoots was detected.

EXAMPLE 2

Transformation of Pineapple Heterogeneous Composite Line (Comprising a Mixture of 1C, 2C, 2A, 3A, and 4A) Using *Agrobacterium tumefaciens* Strain C58pmp9O/pNPT0502, C58pmp9O/pNPT0403, or C58pmp9O/pNPT0402.

1. Preparation of source tissues
   (i) Establishment of shoot cultures.
   Same as Example 1.
   ii) Production of embryogenic cell clusters (ECC).
   Same as Example 1.

2. *Agrobacterium tumefaciens* culture and preparation.

Same as Example 1 except that also *Agrobacterium tumefaciens* strain C58pmp90/pNPT0403, or C58pmp90/pNPT0402 at $OD_{550nm}$ of 0.2 were used for inoculation. pNPT0402 contains the ubiquitin 1 promoter driving the neomycinphosphotransferase II gene and the ubiquitin 1 promoter driving the surB gene. In pNPT0403 plasmid the surB gene is in the opposite direction relative to the NPT II gene.

3. Cocultivation on cocultivation medium.

Same as Example 1 except that 0.7 gm/treatment of ECC was used.

4. Recovery and selection.

After cocultivation, C58pmp90/pNPT0502-inoculated tissues were transferred (Example 1) to selection medium BacPic10ABA.05Cef5OO medium containing either 5 (G5) or 10 (G10) mg/l geneticin for 3 weeks, then to BacPic10ABA.05Cef5OOG30 with 3–4 weeks subculturing intervals for two months, and finally to BacPic10ABA.05Cef100G30 for selection and maintenance. The C58pmp90/pNPT0403- and C58pmp90/pNPT0402-inoculated tissues were transferred (Example 1) to selection medium BacPic10ABA.05Cef500 medium containing either 5 (CS5) or 10 (CS10) μg/l chlorsulfuron for 3 weeks, then to BacPic10ABA.05Cef500CS30 for one month, and finally to BacPic10ABA.05Cef100CS30 and BacPic10ABA.05Cef100G30 for confirmation of transformation.

5. Confirmation of putative transformed tissues.

Same as Example 1. C58pmp90/pNPT0502-inoculated tissues were assayed for gus expression. About 25 independent transgenic callus lines were confirmed for transformation. The CS resistant tissues obtained from the C58pmp90/pNPT0403- and C58pmp90/pNPT0402-inoculated tissues were also tested for resistance to G418. 25–30 independent transgenic callus lines were confirmed for transformation.

6. Production of globular embryos and regeneration of transgenic shoots.

Same as Example 1, except that the resistant ECC tissues were transferred to embryo (FET) formation media BacP10S60, BacP10S6OG30, or BacP10S60CS30 then to maturation media MSS60B.2 or MSS60B.5N.2 media for additional 4 weeks. 16 out of 26 ECC lines tested for regeneration have produce mature embryos.

7. Micropropogation and production of transgenic plants.
   Same as Example 1.

8. Confirmation of transformation.
   Same as Example 1.

EXAMPLE 3

Transformation of Pineapple 1C using *Agrobacterium tumefaciens* strain C58pmp90/pNPT0402.

1. Preparation of ECC as source tissues.
   (i) Establishment of shoot cultures.
   Same as Example 1.
   (ii) Production of embryogenic cell clusters (ECC)
   Same as Example 1.

2. *Agrobacterium tumefaciens* culture and preparation.

Same as Example 1 except that *Agrobacterium tumefaciens* strain C58pmp90/pNPT0402 at $OD_{550nm}$ of 0.2 was used for inoculation.

3. Cocultivation on cocultivation medium.

Same as Example 1 except that 1–1.5 gm/treatment of ECC was used.

4. Recovery and selection.

After cocultivation, tissues were transferred (Example 1) to selection medium BacPic10ABA.05Cef500 containing either 0 (CS0), 3 (CS3), 5 (CS5), or 10 (CS10) μg/l chlorsulfuron for 8 days, followed by transfer to BacPic10ABA.05Cef500CS10 (for CS0, CS5, CS10) or BacPic10ABA.05Cef500CS5 (for CS3) for 4 weeks, and then were all transferred to BacPic10ABA.05Cef500CS20. After one months one or more resistant lines per treatment 3. Cocultivation on cocultivation medium.

Same as Example 1 except that 2 gm/treatment of tissue was used. Also, BacP10As100 was used as cocultivation medium.

4. Recovery and selection.

After cocultivation, tissues were transferred (Example 1) to selection media BacP10Cef500 as presented in Table 4 ("→" indicates subsequent transferral to another selection media). The number in parenthesis refers to the total number of days on the indicated selection media.

TABLE 4

Selection schemes applied for different treatments.

| Agrobacterium | Line | Selection scheme (# days) |
|---|---|---|
| 0402 | 4A | P50(17)→P100 OR 200(21)→G15(24)→CS30(28)→CS10(36)→CS50(28) |
| 0403 | 4A | P50(17)→P100 or 200(21)→G15(24)→CS30(28)→CS10(64) |
| 0502 | 3A | P50(17)→P50, 100 or 200(21)→G15(58)→G30(58) |

(69 for CS0, 9 for CS3, 8 for CS5, and 1 for CS10) were obtained. The resistant ECC lines were transferred to BacS60Cef100CS50 or BacS60Cef100G30 for confirmation and FET formation.

5. Confirmation of putative transformed tissues.

Same as Example 1. The putative resistant ECC lines transferred to BacS60Cef100CS50 or BacS60Cef100G30 were confirmed to be transformed as shown in Table 3.

TABLE 3

Confirmation of putative transformed calli by resistance (res.) to alternative selective agents

| Initial Selection | Total No. | No. tested | Res. to either | CS50 res. | G30 res. |
|---|---|---|---|---|---|
| CS0 | 69 | 38 | 29 | 26 | 17 |
| CS3 | 9 | 9 | 6 | 5 | 4 |
| CS5 | 8 | 8 | 8 | 8 | 8 |
| CS10 | 1 | 1 | 1 | 1 | 1 |

6. Production of globular embryos and regeneration of transgenic shoots.

Same as Example 2, except that the resistant ECC tissues were transferred to embryo (FET) formation media BacS60Cef100CS50 or BacS60Cef100G30.

7. Micropropogation and production of transgenic plants.

Same as Example 2.

8. Confirmation of transformation.

Same as Example 1.

EXAMPLE 4

Transformation of Pineapple 3A and 4A Using *Agrobacterium tumefaciens* strain C58pmp90/pNPT0402, C58pmp90/pNPT0403, and C58pmp90/pNPT0502.

1. Preparation of source tissues: ET and FC.
  (i) Establishment of shoot cultures.
  Same as Example 1.
  (ii) Production of ET and FC.
  Same as Example 1 except that a mixture of ET and FC were used as a source tissue for inoculation.

2. *Agrobacterium tumefaciens* culture and preparation.

Same as Example 1 except that *Agrobacterium tumefaciens* strain C58pmp90/pNPT0402 (0402), C58pmp90/pNPT0403 (0403) and C58pmp90/pNPT0502 (0502) at $OD_{550nm}$ of 0.2 were used for inoculation.

After a total of 5 months 3–50 resistant lines per treatment (20 for 0402 treatment, 50 for 0403 treatment, and 3 for 0502 treatment) were obtained. The delay for the effective selection in this example was due to the long delay (38 days (21+17 days) of P50, P100, or P200 paromomycin treatment).

5. Confirmation of putative transformed tissues.

Same as Example 1. The putative G418-resistant 0402 and 0403 lines were transferred to BacP10Cef100CS30 or CS50 and the putative G418-resistant 0502 line were GUS assayed for confirmation.

6. Production of globular embryos and regeneration of transgenic shoots.

Same as Example 2, except that the resistant tissues were transferred to embryo (FET) formation media BacS60P10 or BacS60P10G30 for 18 weeks followed by transfer on MSB3N.2 medium for 7 weeks then on MSB1 for 4–12 weeks.

EXAMPLE 5

Transformation of Pineapple 1C using *Agrobacterium tumefaciens* strain C58pmp90/pALS 1303.

1. Preparation of ECC as source tissues.
  (i) Establishment of shoot cultures.
  Same as Example 1.
  (ii) Production of embryogenic cell clusters (ECC).
  Same as Example 1.

2. *Agrobacterium tumefaciens* culture and preparation.

Same as Example 1 except that *Agrobacterium tumefaciens* strain C58pmp90/pALS1303 at $OD_{550nm}$ of 0.2 was used for inoculation. pALS1303 contains the Smas promoter (construct no. 5 of Ni et al., 1995, The Plant Jounal 7:661–676) driving the gus gene, and ubiquitin 1 promoter (Christensen et al., 1992, P1. Mol. Biol., 18:675–689) driving the surB gene.

3. Cocultivation on cocultivation medium.

Same as Example 1 except that 3.4 gm of ECC was used.

4. Recovery and selection.

After cocultivation, it was shown that the rate of DNA delivery by GUS assays was extremely low. Nevertheless, tissues were transferred (Example 1) to selection medium BacPic10ABA.05Cef500CS3. After 22 days on CS3, 96 putative CS-resistant lines were obtained. The putative CS-resistant lines then were transferred to BacPic10ABA.05Cef150CS10 for 40 days and to BacPic10ABA.05Cef150CS20 for 34 days. The resistant ECC lines were then transferred to BacPic10S60Cef150CS20 or CS30 for confirmation and FET formation.

5. Confirmation of putative transformed tissues.

Same as Example 1. To date 5 lines have been confirmed by GUS to be fully transformed.

6. Production of globular embryos and regeneration of transgenic shoots.

Same as Example 2.

EXAMPLE 6

Transformation of Pineapple 1C Using *Agrobacterium tumefaciens* Strain C58pmp90/pALS1303.

1. Preparation of ECC as source tissues.
   (i) Establishment of shoot cultures.
   Same as Example 1.
   (ii) Production of embryogenic cell clusters (ECC).
   Same as Example 1.
2. *Agrobacterium tumefaciens* culture and preparation.
   Same as Example 1 except that *Agrobacterium tumefaciens* strain C58pmp90/pNPT0502 at $OD_{550nm}$ of 0.2 was used for inoculation.
3. Cocultivation on cocultivation medium.
   Same as Example 1 except that 0.66 gm of ECC was used.
4. Recovery and selection.
   After a 3-day cocultivation, it was shown that the rate of DNA delivery by GUS assay was extremely low. Nevertheless, tissues were transferred (Example 1) to selection medium BacPic10ABA.05Cef500G10 for 25 days then to BacPic10ABA.05Cef500G30. The resistant ECC lines were then transferred to BacPic10S60Cef100G30 for confirmation and FET formation.
5. Confirmation of putative transformed tissues.
   Same as Example 1. To date one line has been confirmed by GUS to be fully transformed.
6. Production of globular embryos and regeneration of transgenic shoots.
   Same as Example 2, except that tissues were placed on MSB3N.2 for 5 weeks then on BacGB1 for shoot formation.

EXAMPLE 7

Transformation of Pineapple 1C Using *Agrobacterium tumefaciens* Strain C58pmp90/pDEE200 or EHA101/pDEE200.

1. Preparation of source tissues.
   (i) Establishment of shoot culture
   Same as Example 1.
   (ii) Production of leaf bases and core sections.
   Shoots or shoot buds were used as explants. Shoots or buds were cut longitudinally (Example 1) and pretreated (cultured) on MSB3 or MCMP10T0.5 medium for 6 days. Tips of the long leaves (>15 mm) were cut off to provide smaller explants. Leaves were isolated individually to produce 7–10 mm leaf bases and mixed with Agrobacterium for cocultivation. Also, cores were cut into 3–5 mm sections and mixed with Agrobacterium for cocultivation.
2. *Agrobacterium tumefaciens* culture and preparation.
   *Agrobacterium tumefaciens* strain C58pmp90/pDEE200 or EHA101/pDEE200 at $OD_{550nm}$ of 0.3–0.4 was used for inoculation. pDEE200 contains the cauliflower mosaic virus 35S promoter driving surB gene, which confers chlorsulfaron resistance, and the 35S promoter driving the β-glucuronidase (gus) gene as a reporter gene to verify transformation in the plant cells. Acetosyringone (20 μM) was added to the Agrobacterium suspension before inoculation.
3. Cocultivation on cocultivation medium.
   Same as Example 1 except that cocultivation medium was MSTDZ0.5IBA0.5As100. Cocultivation period was 2 days for EHA101—and 3 days for C58pmp90-treated tissues.
4. Recovery and selection.
   After cocultivation, it was shown that the rate of DNA delivery by GUS assays was higher in 3-day cocultivated tissues than 2-day cocultivated tissues (Table 5).

TABLE 5

| | The rate of DNA delivery to leaf bases and core sections of pineapple | | | |
|---|---|---|---|---|
| | 2-day cocultivation | | 3-day cocultivation | |
| Pretreatment | EHA101 | C58pmp90 | EHA101 | C58pmp90 |
| MSB3 | 1/15 | 0/5 | — | 22/17 |
| MCMP10T0.5 | 0/10 | 0/10 | 77/19 | 59/18 |

No. of GUS stained blue spots or patches per total no. of explants are indicated.

Tissues were transferred to selection medium MCMP10T2.2Carb500CS2, 5, or 10 for 10 days and to CS10, 50 or 100 thereafter. After 19 days tissues were transferred to BacP10T2.2Carb500CS3 or CS10. Chimeric shoots were recovered after 3 months on these media.

5. Confirmation of putative transformed tissues.
   Same as Example 1. Shoots from three lines were confirmed by GUS to be chimeric (most of the shoots were stained blue).
6. Production of transgenic shoos.
   Shoots were regenerated on BacP10T2.2Carb500CS3 or CS10 media.

EXAMPLE 8

Transformation of Pineapple 2C using *Agrobacterium tumefaciens* strain LBA4404/pDEE200 or EHA101/pDEE200.

1. Preparation of source tissues.
   (i) Establishment of shoot cultures.
   Same as Example 1.
   (ii) Production of leaf bases and core sections.
   Same as Example 7 except that no pretreatment was done.
2. *Agrobacterium tumefaciens* culture and preparation.
   Same as Example 7 except that *Agrobacterium tumefaciens* strain LBA4404/pDEE200 or EHA101/pDEE200 at $OD_{550nm}$ of 0.4 was used for inoculation.
3. Cocultivation on cocultivation medium.
   Same as Example 7 except that cocultivation was done for 3 or 6 days.
4. Recovery and selection.
   After cocultivation, it was shown that the rate of DNA delivery by GUS assays was very low; i.e. 2–3 spots per 10 explants inoculated. Tissues were transferred to selection media (20–25 explants/plate) to MSTDZ0.5IBA0.5Carb500CS20, 50, or 100 for 10 days and to CS10, 50 or 100, based on their size. After 7 days most tissues turned brown and half of the healthy tissues were transferred to MSTDZ0.5IBA0.5Carb500CS10 for 22 days then to MCMP10CS10, 20, or 50 thereafter. Putative chimeric tissues were transferred to BacP10T2.2Carb500CS3 or BacP10Carb500CS3 or BacP10Carb500CS5. Chimeric shoots were recovered after 3 months on these media: One line from EHA101-treated tissues survived the selection CS100-CS10-CS5 was chimeric and one out of 3 lines from LBA4404-treated tissue survived the selection CS50-CS100-CS3 was chimeric.

5. Confirmation of putative transformed tissues.

Same as Example 1. Shoots from two lines (one per Agrobacterium treatment:) were confirmed by GUS to be chimeric (most of the shoots were stained blue).

6. Production of transgenic shoots.

Shoots were regenerated on BacP10T2.2CS3 or BacP10CS5 media.

EXAMPLE 9

Transformation of Smooth Cayenne Pineapple 1C Using *Agrobacterium tumefaciens* Strain C58pmp90/pDEE200.

1. Preparation of source tissues.
   (i) Establishment of shoot cultures.
   Same as Example 1.
   (ii) Production of leaf bases and core sections.
Same as Example 7 except that pretreatment medium was 1/2MSB3, MCMP10, or MCMP10TDZ1.

2. *Agrobacterium tumefaciens* culture and preparation.

Same as Example 7 except that only *Agrobacterium tumefaciens* strain C58pmp90/pDEE200 was used for inoculation.

3. Cocultivation on cocultivation medium.

Same as Example 7 except that cocultivation was done for 2 or 5 days at 28° C. in the dark.

4. Recovery and selection.

Same as Example 7. After cocultivation, tissues were transferred to selection media MCMP10TDZ2.2Carb500CS3 or 5 for 10–15 days. Embryogenic tissues were cut off the original explants and transferred to BacP10Carb500CSO, 10, or 25. Putative chimeric tissues were transferred to BacP10Carb500CS10 or 20 every 3 weeks. One line produced chimeric shoots after a total of 70 days on selection media as follow: CS3-Cs10-CS20.

5. Confirmation of putative transformed tissues.

Same as Example 1. Shoots from one lines were confirmed by GUS to be chimeric (most of the shoots were stained blue).

6. Production of transgenic shoots.

Shoots were regenerated on BacP10Carb500CS10 medium for 4 weeks followed by transfer on MSB1 medium for 4–6 weeks.

Media Compositions and Abbreviations

AS=acetosyringone; BA (6-BA)=6-benzylaminopurine; 2,4-D=2,4-dichlorophenoxyacetic acid; GA3 =gibberellic acid; geneticin=G418; GUS=6-glucuronidase; HPT=hygromycin phosphotransferase gene; IAA=indole-3-acetic acid; MES= 2-N morpholino ethanesulfonic acid; NAA= naphthaleneacetic acid; Gel-rite (Scott Lab, Inc., Warwick, R.I., USA); MS salts (JRH Bioscience, Lenexa, Kans., USA); BacP=BacPic.

| Minimal A = MinA | | |
| --- | --- | --- |
|  | Preferred | Range |
| potassium phosphate dibasic | 10.5 g/l | 5–20 g/l |
| potassium phosphate monobasic | 4.5 g/l | 2–8 g/l |
| ammonium sulfate | 1.0 g/l | 0.5–3 g/l |
| sodium citrate dihydrate | 0.5 g/l | 0–2 g/l |
| magnesium sulfate heptahydrate | 247 mg/l | 0–1000 g/l |
| glucose | 2.0 g/l | 1–30 g/l |

MinAsuc

MinA but with sucrose instead of glucose.

| L-Broth | |
| --- | --- |
| Tryptone | 10 g/l |
| Yeast Extract | 5 g/l |
| NaCl | 5 g/l |
| Glucose | 1 g/l |
| pH | 7.0–7.2 |
| Bacto Agar | 15 g/l |

For tissue culture media, the pH should be 5–7.5, preferably 5.7. The medium is used following sterilization by autoclaving, except for specific components that are filter-sterilized and then added following autoclaving.

| MS | |
| --- | --- |
| MS salts | 1X |
| B5 vitamins | 1X |
| Sucrose | 30 g/l |
| MES | 600 mg/l |
| Gel-rite ® | 2.5 g/l |
| pH | 5.7 |
| B2N2 | |
| MS medium + | 2 mg/l |
| BA | |
| NAA | 2 mg/l |
| B1.5N.5 | |
| MS medium + | 1.5 mg/l |
| BA | |
| NAA | 0.5 mg/l |
| Bac | |
| Bac major salts | 1X |
| MS minor salts | 1X |
| MS Iron Mix | 1X |
| Bac Vitamins | 1X |
| MES | 600 mg/l |
| Sucrose | 30 g/l |
| Gel-rite ® | 2.0 g/l |
| pH | 5.7 |
| Bac Major Salts: | |
| NH$_4$Cl | 535 mg/l |
| KNO$_3$ | 2528 mg/l |
| CaCl$_2$.2H$_2$O | 440 mg/l |
| MgSO$_4$.7H$_2$O | 370 mg/l |
| KH$_2$PO$_4$ | 170 mg/l |
| Bactris Vitamins: | |
| Thiamine.HCl | 40 mg |
| Pyridoxine.HCl | 50 mg |
| Nicotinic Acid | 50 mg |
| myo-Inositol | 10 g |
| Bac P1 | |
| Bac + | 1 mg/ml |
| Picloram | |
| BacP10 | |
| Bac + | 10 mg/l |
| Picloram | |
| BacS60Z.5 | |
| Bac + | 30 g/l |
| Sucrose | |
| Zeatin | 0.5 mg/l |
| BacP10ABA.05As100 | |
| Bac + | 10 mg/l |
| Picloram | |
| Abscisic acid | 0.05 mg/l |
| Acetosyringone | 20 mg/l |

| | | |
|---|---|---|
| BacP10ABA.05Cef500CS5 | | |
| Bac + | 10 | mg/l |
| Picloram | | |
| Abscisic acid | 0.05 | mg/l |
| Cefotaxime | 500 | mg/l |
| Chlorsulfuron | 5 | μg/l |
| BacP10ABA.05Cef500CS20 | | |
| Bac + | 10 | mg/l |
| Picloram | | |
| Abscisic acid | 0.05 | mg/l |
| Cefotaxime | 500 | mg/l |
| Chlorsulfuron | 20 | μg/l |
| BacP10Carb500 | | |
| BacP10 + | 500 | mg/l |
| Carbenicillin | | |
| BacP10Cef500 | | |
| BacP10 + | 500 | mg/l |
| Cefotaxime | | |
| BacP10CS100Carb500 | | |
| BacP10Carb500 + | 100 | μg/l |
| Chlorsulfuron | | |
| BacP10CS25 | | |
| BacP10 + | 25 | μg/l |
| Chlorsulfuron | | |
| BacP10CS50 | | |
| BacP10 + | 50 | μg/l |
| Chlorsulfuron | | |
| BacP10T2.2CS3 | | |
| BacP10 + | 2.2 | mg/l |
| Thidiazuron | | |
| Chlorsulfuron | 3 | μg/l |
| BacP10CS5 | | |
| BacP10 + | 5 | μg/l |
| Chlorsulfuron | | |
| BacS60B3N.2CS20 | | |
| Bac + | 30 | g/l |
| Sucrose | | |
| BA | 3 | mg/l |
| NAA | 0.2 | mg/l |
| Chlorsulfuron | 20 | μg/l |
| BacB3N.2CS20 | | |
| Bac + | 3 | mg/l |
| BA | | |
| NAA | 0.2 | mg/l |
| Chlorsulfuron | 20 | μg/l |
| BacGS60P10CS20 | | |
| Bac + | | |
| Bac organics | | |
| Sucrose | 30 | g/l |
| Picloram | 10 | mg/l |
| Chlorsulfuron | 20 | μg/l |
| Bactris organics | | |
| Casein hydrolysate | 500 | mg/l |
| Glutamine | 1000 | mg/l |
| Arginine | 120 | mg/l |
| Glycine | 2 | mg/l |
| BacP10S60 | | |
| Bac + | 10 | mg/l |
| Picloram | | |
| Sucrose | 30 | g/l |
| BacP10S60G30 | | |
| BacP10S60 + | 30 | mg/l |
| Geneticin (G418) | | |

| | | |
|---|---|---|
| BacP10S60CS30 | | |
| BacP10S60 + | 30 | μg/l |
| Chlorsulfuron | | |
| BacP10ABA.05 | | |
| Bac + | 10 | mg/l |
| Picloram | | |
| ABA | 0.05 | mg/l |
| BacP10ABA.05Cef500 | | |
| BacP10ABA.05 + | 500 | mg/l |
| Cefotaxime | | |
| BacP10ABA.05Cef500G10 | | |
| BacP10ABA.05Cef500 + | 10 | mg/l |
| Geneticin (G418) | | |
| BacP10ABA.05Cef500G15 | | |
| BacP10ABA.05Cef500 + | 15 | mg/l |
| Geneticin (G418) | | |
| BacP10ABA.05Cef500G30 | | |
| BacP10ABA.05Cef500 + | 30 | mg/l |
| Geneticin (G418) | | |
| BacP10ABA.05Cef500CS3 | | |
| BacP10ABA.05Cef500 + | 3 | μg/l |
| Chlorsulfuron | | |
| BacP10ABA.05Cef500CS30 | | |
| BacP10ABA.05Cef500 + | 30 | μg/l |
| Chlorsulfuron | | |
| BacP10ABA.05Cef100CS30 | | |
| BacP10ABA.05 + | 100 | mg/l |
| Cefotaxime | | |
| Chlorsulfuron | 30 | μg/l |
| BacP10ABA.05Cef150CS10 | | |
| BacP10ABA.05 + | 150 | mg/l |
| Cefotaxime | | |
| Chlorsulfuron | 10 | μg/l |
| BacP10ABA.05Cef150CS20 | | |
| BacP10ABA.05 + | 150 | mg/l |
| Cefotaxime | | |
| Chlorsulfuron | 20 | μg/l |
| BacP10ABA.05Cef100CS50 | | |
| BacP10ABA.05 + | 100 | mg/l |
| Cefotaxime | | |
| Chlorsulfuron | 50 | μg/l |
| BacP10ABA.05Cef100G30 | | |
| BacP10ABA.05 + | 100 | mg/l |
| Cefotaxime | | |
| Geneticin (G418) | 30 | mg/l |
| B1CS20 | | |
| MS + | 1 | mg/l |
| BA | | |
| Chlorsulfuron | 20 | μg/l |
| MSB3N.2 | | |
| MS + | 3 | mg/l |
| BA | | |
| NAA | 0.2 | mg/l |
| ½MSB3 | | |
| same as MS but with ½ salts strength + BA | 3 | mg/l |
| MSS60B3N.2 | | |
| MS + | 3 | mg/l |
| BA | | |
| NAA | 0.2 | mg/l |
| Sucrose | 30 | g/l |

MSS60B.5N.2

| | |
|---|---|
| MS + | 0.5 mg/l |
| BA | |
| NAA | 0.2 mg/l |
| Sucrose | 30 g/l |

MSS60B3N.2

| | |
|---|---|
| MS + | 3 mg/l |
| BA | |
| NAA | 0.2 mg/l |
| Sucrose | 30 g/l |

MSB3N.2Carb500

| | |
|---|---|
| MS + | 3 mg/l |
| BA | |
| NAA | 0.2 mg/l |
| Carbenicillin | 500 mg/l |

MSB3N.2CS20

| | |
|---|---|
| MSB3N.2 + | 20 µg/l |
| Chlorsulfuron | |

MSB1Agar1%

| | |
|---|---|
| MS + | 1 mg/l |
| BA | |
| Agar (instead of Gel-rite) | 10 g/l |

MSB1 liquid

| | |
|---|---|
| MS without Gel-rite + | 1 mg/l |
| BA | |

MSB1

| | |
|---|---|
| MS + | 1 mg/l |
| BA | |

MSB1.5N.5 liquid

| | |
|---|---|
| MS without gel-rite + | 1.5 mg/ml |
| BA | |
| NAA | 0.5 mg/ml |

MSB3

| | |
|---|---|
| MS + | 3 mg/l |
| BA | |

MSP10

| | |
|---|---|
| MS + | 10 mg/l |
| Picloram | |

MSP10TDZ2.2

| | |
|---|---|
| MS + | 10 mg/l |
| Picloram | |
| Thidiazuron | 2.2 mg/l |

MSTDZ.5IBA.5

| | |
|---|---|
| MS + | 0.5 mg/l |
| Thidiazuron | |
| IBA | 0.5 mg/l |

MSTDZ.5IBA.5Carb500CS20

| | |
|---|---|
| MS + | 0.5 mg/l |
| Thidiazuron | |
| IBA | 0.5 mg/l |
| Carbenicillin | 500 mg/l |
| Chlorsulfuron | 20 µg/l |

MSP10TDZ1.1

| | |
|---|---|
| MS + | 10 mg/l |
| Picloram | |
| Thidiazuron | 1.1 mg/l |

MSP10TDZ2.2Suc60

| | |
|---|---|
| MS + | 10 mg/l |
| Picloram | |
| Thidiazuron | 2.2 mg/l |
| Sucrose | 30 g/l |

MSP10TDZ2.2Agar

| | |
|---|---|
| MS + | 6 g/l |
| Agar instead of gelrite | |

| | |
|---|---|
| Picloram | 10 mg/l |
| Thidiazuron | 2.2 mg/l |

MSP10B.5

| | |
|---|---|
| MS + | 10 mg/l |
| Picloram | |
| BA | 0.5 mg/l |

N.5IBA.5 liquid

| | |
|---|---|
| MS without Gel-rite + | 0.5 mg/l |
| NAA | |
| IBA | 0.5 mg/l |

MCM

| | |
|---|---|
| MCM Major Salts | 1X |
| MS Minor | 1X |
| MS Iron Mix | 1X |
| MS Vitamin | 1X |
| Cycad Organics | 1X |
| MES | 600 mg/l |
| Gel-rite ® | 2.2 g/l |
| pH | 5.7 |

MCM Major Salts

| | |
|---|---|
| NH$_4$NO$_3$ | 800 mg |
| KNO$_3$ | 3.032 g |
| CaCl$_2$.2H$_2$O | 440 mg |
| MgSO$_4$.7H$_2$O | 370 mg |
| KH$_2$PO4 | 170 mg |

Cycad Organics

| | |
|---|---|
| Glutamine | 400 mg |
| Ascorbic Acid | 100 mg |
| Casein Hydrolysate | 100 mg |
| Arginine | 100 mg |
| Asparagine | 100 mg |

MCMP10

| | |
|---|---|
| MCM + | 10 mg/l |
| Picloram | |

MCMP10B.5

| | |
|---|---|
| MCM + | 10 mg/l |
| Picloram | |
| BA | 0.5 mg/l |

MCMP10T.5

| | |
|---|---|
| MCM + | 10 mg/l |
| Picloram | |
| Thidiazuron | 0.5 mg/l |

MCMP10T1

| | |
|---|---|
| MCM + | 10 mg/l |
| Picloram | |
| Thidiazuron | 1 mg/l |

MCMP10As100

| | |
|---|---|
| MCM + | 10 mg/l |
| Picloram | |
| Acetosyringone | 20 mg/l |

MCMDi50B.5

| | |
|---|---|
| MCM + | 50 mg/l |
| Dicamba | |
| BA | 0.5 mg/l |

MCMDi10

| | |
|---|---|
| MCM + | 10 mg/l |
| Dicamba | |

MCMP10Carb500CS100

| | |
|---|---|
| MCM + | 10 mg/l |
| Picloram | |
| Carbenicillin | 500 mg/l |
| Chlorsulfuron | 100 µg/l |

MCMP1TDZ2.2

| | |
|---|---|
| MCM + | 1 mg/l |
| Picloram | |
| Thidiazuron | 2.2 mg/l |

-continued

| MCMP1TDZ1.1 | |
|---|---|
| MCM + | |
| Picloram | 1 mg/l |
| Thidiazuron | 1.1 mg/l |

All publications and patents mentioned in this specification are herein incorporated by reference into the specification to the same extent as if each individual publication or patent was specifically and individually indicated to be incorporated herein by reference.

What is claimed is:

1. A method for modifying the genotype of a pineapple cell, said method comprising:
    contacting said pineapple cell with Agrobacterium comprising a T-DNA containing a DNA segment, such that said DNA segment is integrated into the genome of said pineapple cell; and
    selecting a pineapple cell comprising said integrated DNA segment wherein said pineapple cell is an embryogenic cell or an embryogenic callus cell.

2. The method of claim 1, wherein said pineapple cell is selected from the group consisting of Smooth Cayenne, Red Spanish, Perolera, Pernambuco, and Primavera.

3. The method of claim 1, wherein said pineapple cell is Smooth Cayenne.

4. The method of claim 1, wherein said Agrobacterium is *Agrobacterium tumefaciens*.

5. The method of claim 1, further comprising the step of regenerating a pineapple plant from said pineapple cell comprising said integrated DNA segment.

6. The method of claim 1, wherein said DNA segment is selected from the group consisting of ACC synthases, ACC oxidases, malic enzymes, malic dehydrogenases, glucose oxidases, chitinases, defensins, expansins, hemicellulases, xyloglucan transglycosylases, apetala genes, leafy genes, knotted-related genes, homeobox genes, Etr-related genes, and ribonucleases.

7. The method of claim 1, wherein said DNA segment is operably linked to a constitutive promoter.

8. The method of claim 1, wherein said DNA segment is operably linked to an inducible promoter.

9. The method of claim 1, wherein said T-DNA comprises a selectable marker.

10. A pineapple cell modified by the method of claim 1.

11. A method for modifying the genotype of a pineapple cell, said method comprising:
    culturing pineapple tissue to produce pineapple embryogenic cells;
    contacting said pineapple embryogenic cells with Agrobacterium comprising a T-DNA containing a DNA segment, such that said DNA segment is integrated into the genome of said pineapple cells; and
    selecting a pineapple cell comprising said integrated DNA segment.

12. The method of claim 11, wherein said pineapple cell is selected from the group consisting of Smooth Cayenne, Red Spanish, Perolera, Pernambuco, and Primavera.

13. The method of claim 11, wherein said pineapple cell is Smooth Cayenne.

14. The method of claim 11, wherein said Agrobacterium is *Agrobacterium tumefaciens*.

15. The method of claim 11, further comprising the step of regenerating a pineapple plant from said cell comprising said integrated gene.

16. The method of claim 11, wherein said DNA segment is selected from the group consisting of ACC synthases, ACC oxidases, malic enzymes, malic dehydrogenases, glucose oxidases, chitinases, defensins, expansins, hemicellulases, xyloglucan transglycosylases, apetala genes, leafy genes, knotted-related genes, homeobox genes, Etr-related genes, and ribonucleases.

17. The method of claim 11, wherein said DNA segment is operably linked to a constitutive promoter.

18. The method of claim 11, wherein said T-DNA comprises a selectable marker.

19. The method of claimant wherein said embryogenic cells are embryogenic cell clusters in friable callus.

20. The method of claim 11, wherein said embryogenic cells are globular callus.

21. A pineapple cell modified by the method of claim 11.

22. The method of claim 11, wherein said pineapple tissue is cultured on a medium comprising an effective amount of a strong auxin.

23. The method of claim 22, wherein said strong auxin is picloram.

24. The method of claim 11, wherein said pineapple tissue is from a pineapple leaf base.

25. A pineapple plant cell comprising an integrated Agrobacterium T-DNA sequence comprising a heterologous gene wherein said cell is produced by the method of claim 1 or claim 11.

26. The pineapple plant cell of claim 25, wherein said heterologous gene is operably linked to a constitutive promoter.

27. The pineapple plant cell of claim 25, wherein said heterologous gene is operably linked to an inducible promoter.

28. The pineapple plant cell of claim 25, wherein said gene is operably linked to a promoter in sense orientation.

29. The pineapple plant cell of claim 25, wherein said heterologous gene is a selectable marker.

30. The pineapple plant cell of claim 25, wherein said pineapple plant cell is a tissue culture cell.

31. The pineapple plant cell of claim 25 which is Smooth Cayenne.

32. A pineapple plant comprising an integrated Agrobacterium T-DNA sequence comprising a heterologous gene wherein said plant is produced by the method of claim 1 or claim 11.

33. The pineapple plant of claim 32, wherein said heterologous gene confers resistance to insects.

34. The pineapple plant of claim 32, wherein said heterologous gene confers resistance to drought.

35. The pineapple plant of claim 32, wherein said heterologous gene confers resistance to nematodes.

36. The pineapple plant of claim 32, wherein said heterologous gene confers resistance to viral disease.

37. The pineapple plant of claim 32, wherein said heterologous gene confers resistance to bacterial disease.

38. The pineapple plant of claim 32 which is Smooth Cayenne.

* * * * *